US005925519A

United States Patent [19]
Jensen et al.

[11] Patent Number: 5,925,519
[45] Date of Patent: Jul. 20, 1999

[54] GENETIC ALTERATIONS ASSOCIATED WITH PROSTATE CANCER

[75] Inventors: Ronald H. Jensen, Livermore, Calif.; Michael L. Cher, Huntington Woods, Mich.

[73] Assignee: The Regents of the University of California, Oakland, Calif.

[21] Appl. No.: 08/657,105

[22] Filed: Jun. 3, 1996

[51] Int. Cl.[6] .............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search .............................. 435/6; 536/23.1, 536/24.3; 935/76, 77, 78

[56] References Cited

U.S. PATENT DOCUMENTS

| | | | |
|---|---|---|---|
| 5,344,760 | 9/1994 | Harvey et al. | 435/7.5 |
| 5,427,910 | 6/1995 | Kamentsky et al. | 435/6 |
| 5,472,842 | 12/1995 | Stokke et al. | 435/6 |
| 5,506,106 | 4/1996 | Croce et al. | 435/6 |
| 5,552,277 | 9/1996 | Nelson et al. | 435/6 |
| 5,658,730 | 8/1997 | McGill et al. | 435/6 |

OTHER PUBLICATIONS

Macoska et al., Cancer Research 54 : 3824–3830 (1994).
Morton et al., Cancer Research 53 : 3585–3590 (1993).
The Oncor Catalog, p. 17 (1992/1993 Edition).
Joos et al., Genes Chromosomes & Cancer 14 : 267–276 (Dec. 1995).
Williams et al., Cancer Genetics and Cytogenetics 85 : 143–152 (Dec. 1995).
Macoska et al., Genes Chromosomes & Cancer 8 : 88–97 (1993).
Trybus et al., Cancer Research 56 (10) : 2263–2267 (May 1996).
Zenklusen et al., Cancer Research 54 : 6370–6373 (1994).
DeGeorges et al., International Journal of Cancer 62 : 724–731 (Sep. 1995).
Brothman et al., Cancer Research 50 : 3795–3803 (1990).
Goffman et al., Cancer Genetics and Cytogenetics 8(3) : 197–202 (1993).
Hasketh, R., "The Oncogene Handbook", p. 493, Academic Press, SanDiego, CA (1994).
Kallionemi et al., PNAS 89 : 5321–5325 (1992).
Bowcock et al., Science 258 : 73 (1992).
M. Chang et al. "Short Communication: Deletion Mapping of Chromosome 8p in Colorectal Carcinoma and Dysplasia Arising in Ulcerative Colitis, Prostatic Carcinoma, and Malignant Fibrous Histiocytomas" *American Journal of Pathology* 144:1–6 (1994).
T. Visakorpi et al. "Genetic Changes in Primary and Recurrent Prostate Cancer by Comparative Genomic Hybridization" *Cancer Research* 55:342–347 (1995).

G.S. Bova et al. "Homozygous Deletion and Frequent Allelic Loss of Chromosome 8p22 Loci in Human Prostate Cancer" *Cancer Research* 53:3869–3873 (1993).
B.S. Carter et al. "Allelic loss of chromosomes 16q and 10q in human prostate cancer" *Proc. Natl. Acad. Sci. USA* 87:8751–8755 (1990).
M.L. Cher et al. "Comparative Genomic Hybridization, Allelic Imbalance, and Fluorescence In Situ Hybridization on Chromosome 8 in Prostate Cancer" *Genes, Chromosomes & Cancer* 11:153–162 (1994).
G. Massenkeil et al. "P53 Mutations and Loss of Heterozygosity on Chromosomes 8p, 16q, 17p, and 18q are Confined to Advanced Prostate Cancer" *Anticancer Research* 14:2789–2794 (1994).
A. Latil et al. "Genetic Alterations in Localized Prostate Cancer: Identification of a Common Region of Deletion on Chromosome Arm 18q" *Genes, Chromosomes & Cancer* 11:119–125 (1994).
S.M.A. Phillips et al. "Loss of heterozygosity of the retinoblastoma and adenomatous polyposis susceptibility gene loci and in chromosomes 10p, 10q and 16q in human prostate cancer" *British Journal of Urology* 73:390–395 (1994).
M.L. Cher et al. "Mapping of Regions of Physical Deletion on Chromosome 16q in Prostate Cancer Cells by Fluorescence In Situ Hybridization (Fish)" *The Journal of Urology* 153:249–254 (1995).
H. Suzuki et al. "Localization of a Tumor Suppressor Gene Associated With Progression of Human Prostate Cancer Within a 1.2 Mb Region of 8p22–p21.3" *Genes, Chromosomes & Cancer* 13:168–174 (1995).
J. Trapman et al. "Loss of Heterozygosity of Chromosome 8 Microsatellite Loci Implicates a Candidate Tumor Suppressor Gene between the Loci D8S87 and D8S133 in Human Prostate Cancer" *Cancer Research* 54:6061–6064 (1994).
D. MacGrogan et al. "Loss of Chromosome Arm 8p Loci in Prostate Cancer: Mapping by Quantitative Allelic Imbalance" *Genes, Chromosomes & Cancer* 10:151–159 (1994).
U.S.R. Bergerheim et al. "Deletion Mapping of Chromosomes 8, 10, and 16 in Human Prostatic Carcinoma" *Genes, Chromosomes & Cancer* 3:215–220 (1991).
W.A. Sakr et al. "Allelic Loss in Locally Metastatic, Multisampled Prostate Cancer" *Cancer Research* 54:3273–3277 (1994).
K. Kunimi et al. "Allelotyping of Human Prostatic Adenocarcinoma" *Genomics* 11:530–536 (1991).

*Primary Examiner*—W. Gary Jones
*Assistant Examiner*—Ethan Whisenant
*Attorney, Agent, or Firm*—Townsend and Townsend and Crew

[57] ABSTRACT

The present invention provides new probes for the detection of prostate cancer cells. The probes bind selectively with target polynucleotide sequences selected from the group consisting of 2q, 4q, 5q, 6q, 10p, 15q, 1q, 2p, 3q, 3p, 4q, 6p, 7p, 7q, 9q, 11p, 16p, and 17q.

12 Claims, 8 Drawing Sheets

GENETIC ALTERATIONS ASSOCIATED WITH PROSTATE CANCER

FIELD OF THE INVENTION

This invention relates to the field of cytogenetics. In particular it provides new diagnostic nucleic acid markers for prostate cancer.

BACKGROUND OF THE INVENTION

Molecular genetic mechanisms responsible for the development and progression of prostate cancer remain largely unknown. Identification of sites of frequent and recurring allelic deletion or gain is a first step toward identifying some of the important genes involved in the malignant process. Previous studies in retinoblastoma (Friend, et al *Nature,* 323:643–6 (1986)) and other cancers (Cawthon, et al., *Cell,* 62:193–201 (1990); Baker, et al., *Science,* 244:217–21 (1989); Shuin, et al., *Cancer Res,* 54:2832–5 (1994)) have amply demonstrated that definition of regional chromosomal deletions occurring in the genomes of human tumors can serve as useful diagnostic markers for disease and are an important initial step towards identification of critical genes. Similarly, regions of common chromosomal gain have been associated with amplification of specific genes (Visakorpi, et al., *Nature Genetics,* 9:401–6 (1995)). Additionally, definition of the full spectrum of common allelic changes in prostate cancer may lead to the association of specific changes with clinical outcome, as indicated by recent studies in colon cancer and Wilms'tumor (Jen, et al., *N. Engl. J. Med.,* 331:213–21 (1994); Grundy, et al., *Cancer Res,* 54:2331–3 (1994)).

Prostate cancer allelotyping studies (Carter, et al., *Proc Natl Acad Sci* USA, 87:8751–5 (1990); Kunimi, et al., *Genomics,* 11:530–6 (1991)) designed to investigate one or two loci on many chromosomal arms have revealed frequent loss of heterozygosity (LOH) on chromosomes 8p (50%), 10p (55%), 10q (30%), 16q (31–60%) and 18q (17–43%). Recently, several groups have performed more detailed deletion mapping studies in some of these regions. On 8p, the high frequency of allelic loss has been confirmed, and the regions of common deletion have been narrowed (Bova, et al., *Cancer Res,* 53:3869–73 (1993); MacGrogan, et al., *Genes Chromosom Cancer,* 10:151–159 (1994); Bergerheim, et al., *Genes Chromosom Cancer,* 3:215–20 (1991); Chang, et al., Am T Pathol, 144:1–6 (1994); Trapman, et al., *Cancer Res,* 54:6061–4 (1994); Suzuki, et al., *Genes Chromosom Cancer,* 13:168-74 (1995)). Similar efforts also served to narrow the region of common deletion on chromosome 16q (Bergerheim, et al., *Genes Chromosom Cancer,* 3:215–20 (1991); Cher, et al., *J Urol,* 153:249–54 (1995)). Other prostate cancer allelotyping studies utilizing a smaller number of polymorphic markers have not revealed new areas of interest (Phillips, et al., *Br J Urol,* 73:390–5 (1994); Sake, et al., *Cancer Res,* 54:3273–7 (1994); Latil, et al., *Genes Chromosom Cancer,* 11:119–25 (1994); Massenkeil, et al., *Anticancer Res,* 14:2785–90 (1994)). At present, allelotyping studies are limited by the low number of loci studied, low case numbers, heterogeneous groups of patients, the use of tumors of low or unclear purity, and lack of standardization of experimental techniques. For these reasons, it has been difficult to compare frequencies of alterations between studies, and we have yet to gain an overall view of regional chromosomal alterations occurring in this disease.

Comparative genomic hybridization (CGH) is a relatively new molecular technique used to screen DNA from tumors for regional chromosomal alterations (Kallioniemi, et al., *Science,* 258:818–21 (1992) and WO 93/18186). Unlike microsatellite or Southern analysis allelotyping studies, which typically sample far less than 0.1% of the total genome, a significant advantage of CGH is that all chromosome arms are scanned for losses and gains. Moreover, because CGH does not rely on naturally occurring polymorphisms, all regions are informative, whereas polymorphism-based techniques are limited by homozygous (uninformative) alleles among a fraction of tumors studied at every locus.

CGH can detect and map single copy losses and gains in prostate cancer with a high degree of accuracy when compared with the standard techniques of allelotyping (Cher, et al., *Genes Chromosom Cancer,* 11:153–162 (1994)). Copy-number karyotype maps have been generated for prostate cancer showing several recurrently altered regions of the genome (Cher, et al., *Genes Chromosom Cancer,* 11:153–162 (1994); Visakorpi, et al., *Cancer Res,* 55:342–347 (1995)).

Although previous studies have begun to reveal a genome-wide view of chromosomal alterations occurring in primary and recurrent prostate cancer, metastatic prostate cancer has not been examined in depth. The present invention addresses these and other needs in the prior art.

SUMMARY OF THE INVENTION

The present invention provides compositions and methods of detecting a genetic alterations correlated with prostate cancer. The methods comprise contacting a nucleic acid sample from a patient with a probe which binds selectively to a target polynucleotide sequence correlated with prostate cancer. The invention provides the following chromosomal regions which are deleted in prostate cancer cells: 2q, 4q, 5q, 6q, 10p, and 15q. Regions which show increases in copy number in prostate cancer cells are: 1q, 2p, 3q, 3p, 4q, 6p, 7p, 7q, 9q, 11p, 16p, and 17q.

The probes of the invention are contacted with the sample under conditions in which the probe binds selectively with the target polynucleotide sequence to form a hybridization complex. The formation of the hybridization complex is then detected.

Alternatively, sample DNA from the patient can be fluorescently labeled and competitively hybridized against fluorescently labeled normal DNA to normal lymphocyte metaphases. Alterations in DNA copy number in the sample DNA are then detected as increases or decreases in sample DNA as compared to normal DNA.

The chromosome abnormality is typically a deletion or an increase in copy number. The methods can be used to detect both metastatic prostate cancers and in androgen independent prostate cancer.

Definitions A "nucleic acid sample" as used herein refers to a sample comprising DNA in a form suitable for hybridization to a probes of the invention. For instance, the nucleic acid sample can be a tissue or cell sample prepared for standard in situ hybridization methods described below. The sample is prepared such that individual chromosomes remain substantially intact and typically comprises metaphase spreads or interphase nuclei prepared according to standard techniques.

The sample may also be isolated nucleic acids immobilized on a solid surface (e.g., nitrocellulose) for use in Southern or dot blot hybridizations and the like. In some cases, the nucleic acids may be amplified using standard techniques such as PCR, prior to the hybridization. The sample is typically taken from a patient suspected of having a prostate cancer associated with the abnormality being detected.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe is labeled as described below so that its binding to the target can be detected. The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the regions of genetic alteration as described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

"Hybridizing" refers the binding of two single stranded nucleic acids via complementary base pairing.

"Bind(s) substantially" or "binds specifically" or "binds selectively" or "hybridizing specifically to" refers to complementary hybridization between a probe and a target sequence and embraces minor mismatches that can be accommodated by reducing the stringency of the hybridization media to achieve the desired detection of the target polynucleotide sequence. These terms also refer to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions will be those in which the salt concentration is at least about 0.02 Na ion concentration (or other salts) at pH 7.0 to 8.3 and the temperature is at least about 60° C. Stringent conditions may also be achieved with the addition of destabilizing agents such as formamide.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85:2444 (1988), by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° C. lower than the thermal melting point $(T_m)$ for the specific sequence at a defined ionic strength and pH. The Tm is the temperature (under defined ionic strength and pH) at which 50% of the target sequence hybridizes to a perfectly matched probe. Typically, stringent conditions will be those as described above.

BRIEF DESCRIPTION OF THE DRAWINGS

FIG. 7A) Gains. FIG. 7B) Losses.

DESCRIPTION OF THE PREFERRED EMBODIMENT

Figure 1:
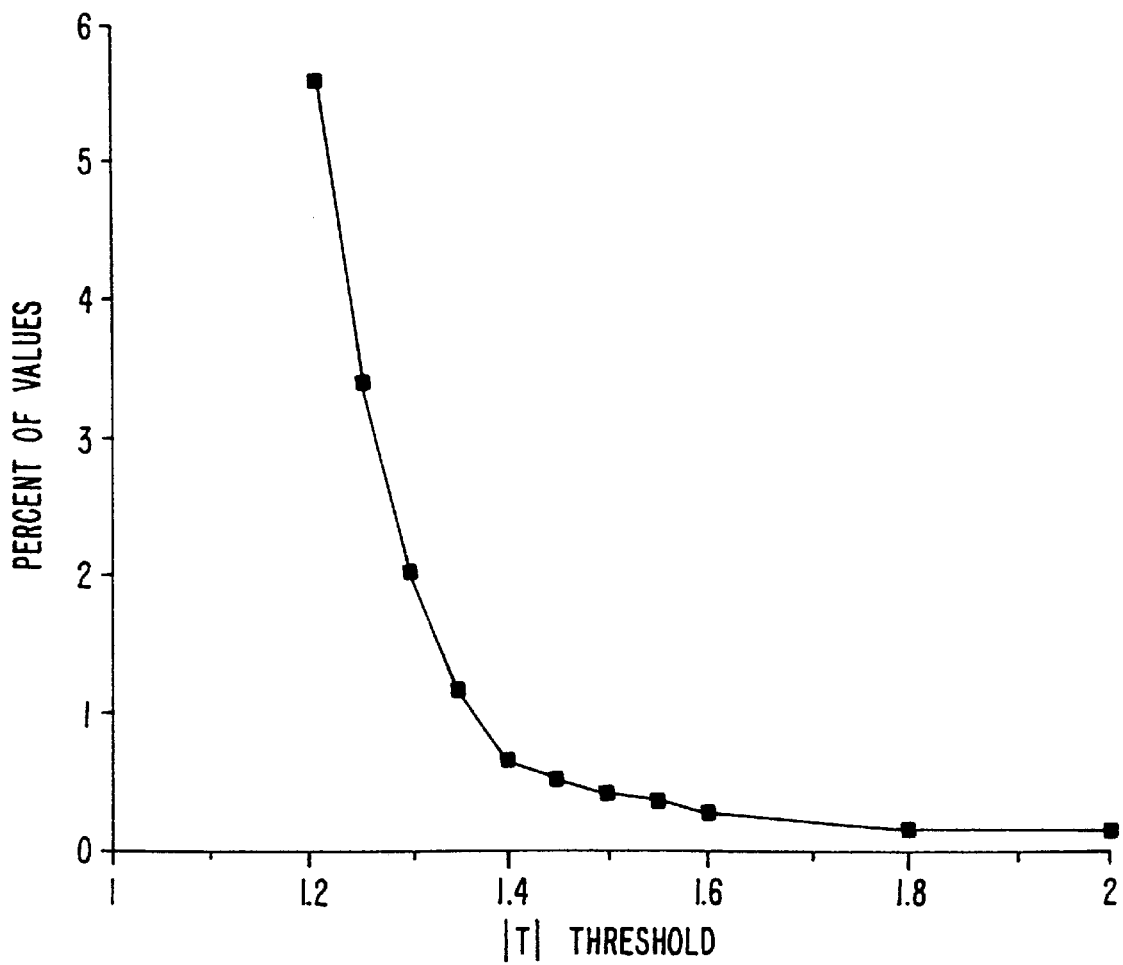
FIG. 1 is a graph illustrating the setting of the t-threshold based on control, normal/normal hybridizations. For 5 control hybridizations, each with 1247 t values extending along the genome from 1 pter to Y qter (a total of 6235 t values), the y axis gives percentage of t values with absolute value greater than the given threshold on the x axis.

The present invention is based on a comprehensive molecular cytogenetic analysis of the genomes of prostate cancer cells using comparative genomic hybridization (CGH). In particular, a new quantitative statistical method of CGH to identify several novel regions of frequent deletion or gain of DNA copy numbers in prostate cancer is provided. The results provided here also help to clarify the relative importance of several other previously reported regions of loss or gain. Modified function of genes contained within the most frequently altered regions may be largely responsible for the malignant behavior of prostate cancer.

Genetic Alterations Associated With Prostate Cancer

Genomic regions that are found to be sites of increased DNA copy number in a large fraction of the cell lines are likely to include oncogenes that are present at increased copy number and hence overexpressed. Overexpression of these genes may lead to uncontrolled growth. Regions that frequently show a decreased DNA copy number may contain tumor suppressor genes that through mutation of one allele and deletion on the other lead to loss of growth or organizational control (Weinberg, *Science* 254:1138–1146 (1992)). Of course, some of the DNA copy number abnormalities may arise as secondary consequences of general genomic instability resulting from the early stages of tumorigenesis. Such alterations are expected to occur randomly and, therefore, are not likely to be found in a high percentage of tumors and cell lines.

In the examples described below, tumors from a set of 31 advanced prostate cancers were used to define genetic alterations involved in both initiation and progression of prostate cancer. CGH analysis was also corroborated with parallel Southern and microsatellite analysis of allelic imbalance on the same DNA. The good agreement between these two analytical techniques provides assurance that the new, standardized CGH analysis is demonstrating high sensitivity and specificity.

In the examples described below, multiple CGH analyses were obtained for each chromosome in each tumor, and a point by point comparison of the mean tumor/normal color ratio to a control normal/normal color ratio in each of 1247 evenly distributed data channels comprising the entire human genome was interpreted as loss, gain, or no change in copy number in the tumor genome.

Group I tissue was obtained from prostate cancer metastases from 20 patients, 19 of whom had received no prior prostate cancer treatment. These samples, which contained highly enriched tumor DNA, showed the high rates of alteration in several chromosomal regions known to be frequently altered in prostate cancer: 8q gain (85%), 8p loss (80%), 13q loss (75%), 16q loss (55%), 17p loss (50%) and 10q loss (50%).

Group II tissue was obtained from 11 patients who had been treated with long term androgen deprivation therapy and developed androgen independent metastatic disease. Quantitative CGH analysis on DNA from these tissues showed chromosomal alterations which were very similar to those found in Group I, suggesting that untreated metastatic tumors contain the bulk of chromosomal alterations necessary for recurrence to occur during androgen deprivation.

In the entire data set, a number of previously undetected regions of frequent loss or gain were identified, including losses of chromosomes 2q (42%), 5q (39%), 6q (39%), and 15q (39%) and gains of chromosomes 11p (52%), 1q (52%), 3q (52%), and 2p (45%).

Figure 7A:
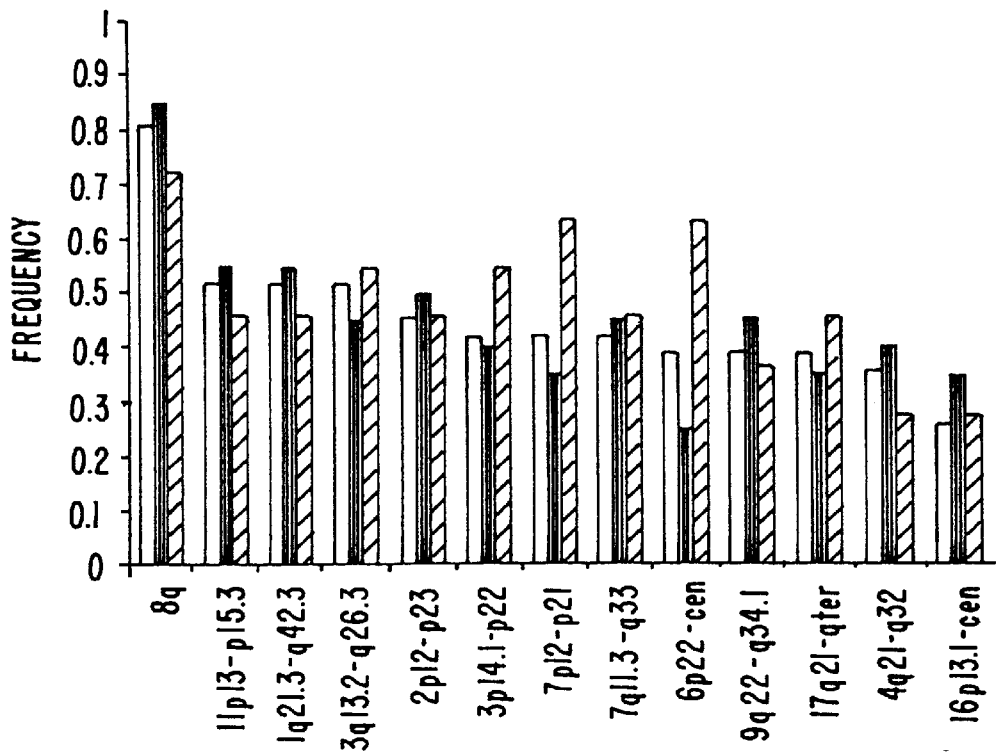
FIGS. 7A and 7B are bar graphs showing a comparison of frequency of alterations of most frequently altered regions for the entire set (open bars); Group I (solid bars); and Group II (shaded bars) specimens.
Figure 7B:
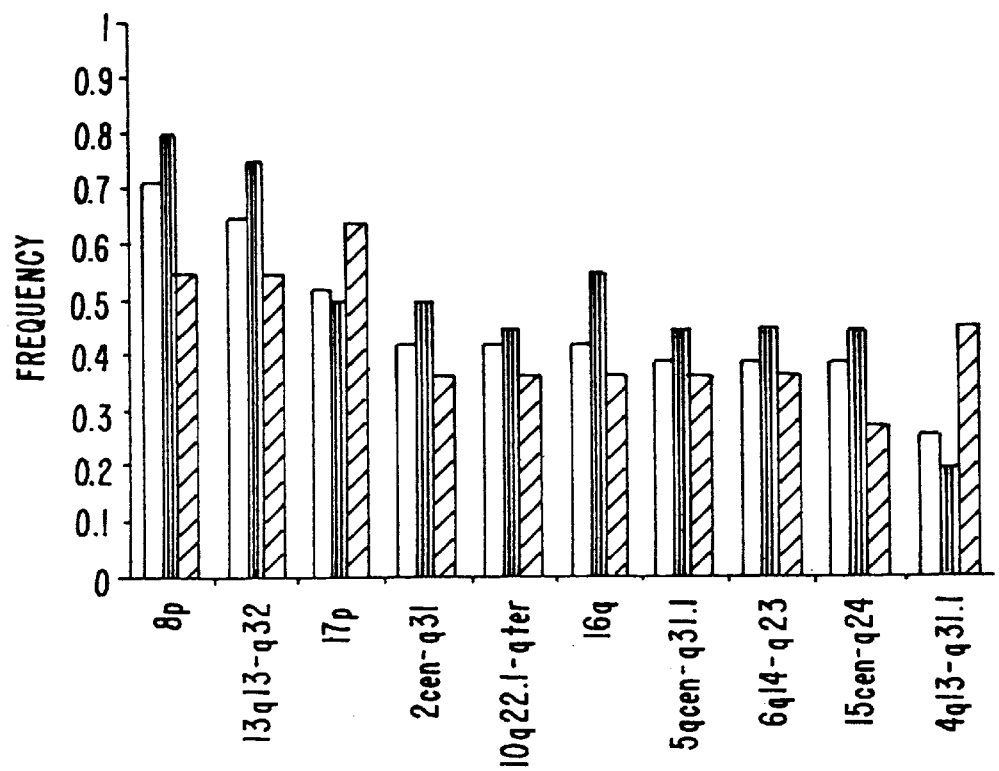

A summary of these results is provided in FIG. 7. As used here, a "region" is at least 5 contiguous channels. A particular abnormality is considered to occur "frequently" if it occurs in greater than 20% of the tumors tested.

Regions of Loss

These regions are suspected to carry at least one recessive oncogene; in fact, many of the most frequently lost regions contain known or candidate tumor suppressor genes. For example the most intensively studied tumor suppressor gene, p53, is located on 17p and previously was shown to be mutated in 20–25% of metastatic prostate cancers (Bookstein, et al., *Cancer Res*, 53:3369–73 (1993)). It also has been reported as mutated in 8/16 (50%) prostate cancer bone marrow metastases (Aprikian, et al., *J. Urol*, 151:1276–80 (1994)) and was shown to suppress in vitro growth of prostate cancer cell lines (Isaacs, et al., *Cancer Res*, 51:4716–20 (1991)). Loss of 17p was detected in 50% of Group I tumors as compared with 65% of Group II tumors. These data taken together support the view that loss of normal p53 function is associated with prostate tumor progression, and it appears to be an alteration which occurs most commonly in late stages of the disease.

Chromosome 10q22.1 -qter contains the candidate tumor suppressor gene Mxil, previously reported to be mutated in four prostate cancer cases (Eagle, et al., *Nature Genetics,* 9:249–255 (1995)). Since the Mxil protein is suspected to repress c-Myc activity (Zervos, et al., *Cell,* 72:223–32 (1993)), loss of Mxii activity may lead to activation of c-Myc. In concert with potential increased chromosome 8q copy number (discussed below), increased c-Myc activity may be a common theme in prostate cancer.

Chromosome 5q contains the alpha catenin gene (5q31) (Furukawa, et al., *Cytogen Cell Genet,* 65:74-8 (1994)), which is a necessary component of the E-cadherin mediated cell adhesion complex. It has previously been shown that five of the six human prostate cancer cell lines have reduced or absent levels of alpha catenin or E-cadherin as compared with normal prostatic epithelial cells (Morton, et al., *Cancer Res,* 53:3585–90 (1993)).

Figure 6A:
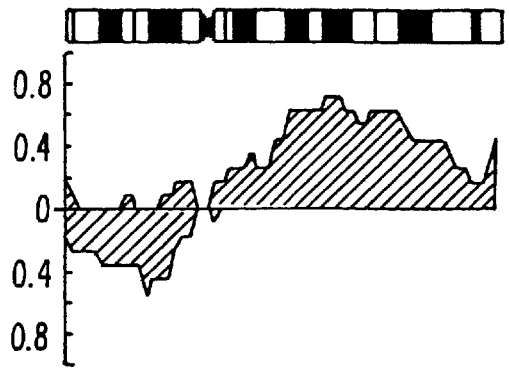
FIG. 6 shows frequency histograms of chromosomal alterations in Group II specimens. Examples of frequency histograms for the two chromosomes most frequently altered in Group II specimens are shown for comparison to Group I (see FIG. 5). The frequency of gains and losses are depicted as described in FIG. 5.
Figure 6B:
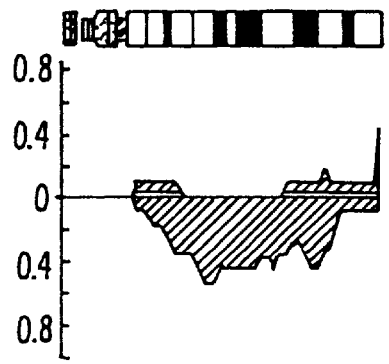
Figure 5I:
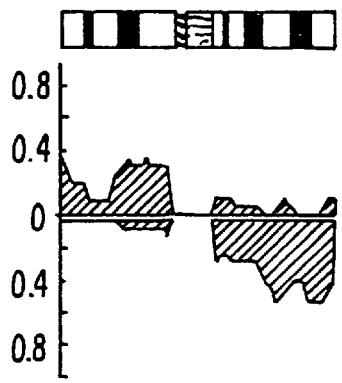
Figure 5J:
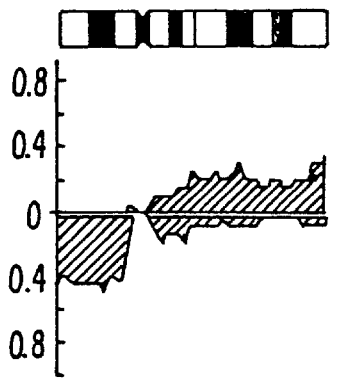

Two other frequently lost regions containing known candidate tumor suppressor genes are chromosome 13q (contains Rb1) and 16q (contains E-cadherin). Interestingly, close analysis of the patterns of loss on these chromosomal arms suggests that more than one important prostate cancer tumor suppressor gene may be located on 13q and 16q. Although the frequency of loss for all 31 tumors studied increases from 40% to 60% across 13q14, where Rb1 is located, the peak appears just distal to 13q14 and is sustained near 60% across 13q21.1-q31 (see FIGS. 5 and 6). While previous studies have shown that loss of Rb1 expression (Bookstein, et al., *Proc Natl Acad Sci* USA, 87:7762–6 (1990)) and allelic loss of this gene (Brooks, et al., Prostate, 26:35–9 (1995)) do occur in prostate tumors, the CGH findings raise the possibility that there is a second important prostate cancer tumor suppressor gene on chromosome 13q distal to Rb1. Similarly, while decreased E-cadherin expression is associated with poor prognosis in prostate cancer (Umbas, et al., *Cancer Res,* 54:3929–33 (1994); Umbas, et al., *Cancer Res,* 52:5104–9 (1992)), and 30% of all 31 tumors in this study show loss in this region; there is a separate region of 40% loss at 16q24 that may signify the site of another important prostate cancer tumor suppressor gene. This regional mapping is in agreement with a previous cosmid deletion mapping study on 16q (Cher, et al., *J Urol,* 153:249–54 (1995)).

The other regions of frequent loss do not possess genes that previously have been identified as candidate tumor suppressor genes. However, the fact that these regions are lost at high frequency in advanced tumors indicates that they detection of these regions is useful in diagnostic and prognostic applications. The evidence also strongly indicates that genes of importance to the progression of this disease may exist at these sites. In particular, there is great interest in the frequent loss of chromosome 8p, and a number of research groups are investigating this region for the presence of an important tumor suppressor gene (Bova, et al., *Cancer Res,* 53:3869–73 (1993); MacGrogan, et al., *Genes Chromosom Cancer,* 10:151–159 (1994); Chang, et al., *Am T Pathol,* 144:1–6 (1994); Trapman, et al., *Cancer Res,* 54:6061–4 (1994); Cher, et al., *Genes Chromosom Cancer,* 11:153–162 (1994); Matsuyama, et al., *Oncogene,* 9:3071–3076 (1994)). Regions 2q, 6q, 10p and 15q also fall into this category. These regions are therefore useful as genetic markers and should be analyzed more extensively for tumor suppressor genes.

Regions of Gain.

In these regions, dominant oncogenes that exhibit increased expression with increased copy number are expected to be found. The most notable of these is chromosome 8q, where the c-Myc oncogene is located. Amplification of this region has previously been shown to be correlated with adverse prognosis in prostate cancer (Van Den Berg, et al., *Clin Ca Res,* 1:11–18 (1993)). The frequency of gain of 8q detected by CGH is much higher than reported previously in smaller, series (Bova, et al., *Cancer Res,* 53:3869–73 (1993); Van Den Berg, et al., *Clin Ca Res,* 1:11–18 (1993)) and may reflect the superior ability to detect gain using CGH.

Chromosome 11p shows gains in 52% of the specimens in the data presented below, and the potent oncogene H-Ras is located at 11p15.5. While this region is not identified as the most common region of gain (11p13-p15.3), CGH is unreliable near telomeres due to fluorescence intensity losses at the termini. Thus, it may be that this oncogene is included in a region frequently gained in advanced prostate cancer. Notably it was determined that 40% (8/20) of the metastases show gains at 11p15.5 (see FIG. 5). While it is possible that this gain in copy number could be responsible for H-Ras activation in prostate cancer, mutation or promoter induction could also induce activation, although previous studies have shown only 3 H-Ras gene mutations in 94 samples analyzed (Isaacs, et al., *Sem Oncol.,* 21;514–21 (1994)).

Another region which contains a known oncogene is chromosome 7p, where erbB-1 (=EGFR) is located. Although it has been shown that trisomy in chromosome 7 is associated with higher grade and stage of prostate cancer (Bandyk, et al., *Genes Chromosom Cancer,* 9:19–27 (1994); Stephenson, et al., *Cancer Res,* 47:2504–7 (1987)), no strong evidence has been published which indicates specific gene(s) on this chromosome that are important to the phenotype.

FIG. 7 shows that chromosome 7q displays gains in up to 40% of the specimens from both the metastases and the androgen independent tumors. Recently, it has been shown that the c-met oncogene, which maps to 7q31, is expressed in the basal epithelial cells of 36/43 primary prostate cancer samples, 4/4 lymph node metastases and 23/23 bone marrow metastases (Pisters, et al., *Journal of Urology,* 154:293–8 (1995)).

FIG. 7 indicates that gains occur at a frequency of 0.39 in a region of chromosome 17q that includes BRCA1, while Gao et al. recently showed frequent PCR-based LOH of BRCA1 on chromosome 17q in prostate cancer (Gao, et al., *Cancer Res,* 55:1002–5 (1995)). Again, these results could be explained by somatic recombination followed by gain, or incorrect interpretation of PCR allelic bands.

The oncogene erbB-2 is located at 17q12, which is in the vicinity of the region of high frequency of gain by CGH. Previously Kuhn et al. have shown that 18/53 clinically localized prostate cancers expressed high levels of this gene with no indications of high level gene amplification (Kuhn, et al. *Journal of Urology* (1993)). It is possible that the modest increase in copy number that is evident in the present analyses is responsible for such increased gene expression.

The androgen receptor gene, located in Xq12, was shown previously to display gains at a relatively high frequency (4/9) in recurrent prostate tumors (Visakorpi, et al., *Cancer Res,* 55:342–347 (1995)). In a subsequent report, Visakorpi et al. showed that amplification of Xq12 is associated with tumor recurrence in individuals during androgen deprivation therapy (Visakorpi, et al., *Nature Genetics,* 9:401–6 (1995)).

Although this region was gained in only 5/31 (16%) of the entire group of tumors studied here it was gained in 3/11 (27%) of the Group II androgen independent tumors. Thus, the present studies are in general agreement with those of Visakorpi et al. and support their suggestion that tumor cells with androgen receptor amplification are selected during androgen deprivation therapy. However, amplification of this region is not restricted to tumors failing hormonal therapy.

African Americans.

The results presented below show increased frequency of gains in the region 4q25-q28 in African Americans ($p<0.001$). A gene could be located on 4q which is more frequently increased in activity and induces more rapid clinical progression of prostate cancer among African-Americans (Pienta, et al., *Urology,* 45:93–101, (1993); Brawn, et al., *Cancer,* 71:2369–73 (1993)).

Detecting Genetic Alterations

Using the results provided here, one of skill can prepare nucleic acid probes specific to particular genomic regions of genetic alteration that are associated with prostate cancer. The probes can be used in a variety of nucleic acid hybridization assays to detect the presence (in particular increased copy number) or absence of the regions for the early diagnosis or prognosis of cancer. As noted above, the probes are primarily useful for the diagnosis or prognosis of prostate cancer. The regions can also be used for a large number of other cancers. These include, but are not limited to breast, ovary, bladder, head and neck, and colon.

The genetic alterations are detected through the hybridization of a probe of this invention to a nucleic acid sample in which it is desired to screen for the alteration. Suitable hybridization formats are well known to those of skill in the art and include, but are not limited to, variations of Southern Blots, in situ hybridization and quantitative amplification methods such as quantitative PCR (see, e.g. Sambrook, *Molecular Cloning—A Laboratory Manual,* Cold Spring Harbor Laboratory, Cold Spring Harbor, N.Y., (1989), Kallioniemi et al., *Proc. Natl Acad Sci* USA, 89: 5321–5325 (1992), and *PCR Protocols, A Guide to Methods and Applications,* Innis et al., Academic Press, Inc. New York, (1990)).

In situ hybridization.

In a preferred embodiment, the regions disclosed here are identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci.* USA, 85: 9138–9142 (1988) and in EPO Pub. No. 430,402. Suitable hybridization protocols can also be found in *Methods o\in Molecular Biology* Vol. 33:*In Situ Hybridization Protocols,* K. H. A. Choo, ed., Humana Press, Totowa, N.J., (1994). In a particularly preferred embodiment, the hybridization protocol of Kallioniemi et al., *Proc. Natl Acad Sci* USA, 89:5321–5325 (1992) is used.

Typically, it is desirable to use dual color FISH, in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet.* 60: 190–193 (1992)). For instance, small biopsy tissue samples from tumors can be used for touch preparations (see, e.g., Kallioniemi, A. et al., *Cytogenet. Cell Genet.* 60: 190–193 (1992)). Small numbers of cells obtained from aspiration biopsy or cells in bodily fluids (e.g., blood, urine, sputum and the like) can also be analyzed.

Southern blots.

In a Southern Blot, a genomic or cDNA (typically fragmented and separated on an electrophoretic gel) is hybridized to a probe specific for the target region. Comparison of the intensity of the hybridization signal from the probe for the target region with the signal from a probe directed to a control (non amplified or deleted) such as centromeric DNA, provides an estimate of the relative copy number of the target nucleic acid. Procedures for carrying out Southern hybridizations are well known to those of skill in the art. see, e.g., Sambrook et al., supra.

Preparation of Probes of the Invention

A number of methods can be used to identify probes which hybridize specifically to the regions identified here. For instance, probes can be generated by the random selection of clones from a chromosome specific library, and then mapped to each chromosome or region by digital imaging microscopy. This procedure is described in U.S. Pat. No. 5,472,842. Briefly, a selected chromosome is isolated by flow cytometry, according to standard procedures. The chromosome is then digested with restriction enzymes appropriate to give DNA sequences of at least about 20 kb and more preferably about 40 kb. Techniques of partial sequence digestion are well known in the art. See, for example Perbal, *A Practical Guide to Molecular Cloning* 2nd Ed., Wiley N.Y. (1988). The resulting sequences are ligated with a vector and introduced into the appropriate host. Exemplary vectors suitable for this purpose include cosmids, yeast artificial chromosomes (YACs), bacterial artificial chromosomes (BACs) and P1 phage. Typically, cosmid libraries are prepared. Various libraries spanning entire chromosomes are also available commercially (Clonetech, South San Francisco, Calif.) or from the Los Alamos National Laboratory.

Once a probe library is constructed, a subset of the probes is physically mapped on the selected chromosome. FISH and digital image analysis can be used to localize clones along the desired chromosome. Briefly, the clones are mapped by FISH to metaphase spreads from normal cells using e.g., FITC as the fluorophore. The chromosomes may be counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere.

The accuracy of the mapped positions of the probes can be increased using interphase mapping. Briefly, the distance between two probes which are found by metaphase mapping to be very close is measured in normal interphase nuclei. The genomic distance between the two is equal to the square of the physical distance (Van den Engh et al, *Science* 257:1410 (1992)). If the order is uncertain, the probes are labeled with different colors and their relative distance to a third (distant) probe can be reassessed. Trask et al., *Am. J. Hum. Genet.* 48:1 (1991).

Typically, a mapped library will consist of between about 20 and about 125 clones, more usually between about 30 and about 50 clones. Ideally, the clones are distributed relatively uniformly across the region of interest, usually a whole chromosome.

Sequence information of the region identified here permits the design of highly specific hybridization probes or amplification primers suitable for detection of the target sequences. This is useful for diagnostic screening systems as well as research purposes. Means for detecting specific DNA sequences are well known to those of skill in the art. For instance, oligonucleotide probes chosen to be complementary to a selected subsequence with the region can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

Labeling Probes

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation or random primer extension (Rigby, et al. *J. Mol. Biol.,* 113:237 (1977) or Sambrook, et al.).

One of skill in the art will appreciate that the probes of this invention need not be absolutely specific for the targeted region of the genome. Rather, the probes are intended to produce "staining contrast". "Contrast" is quantified by the ratio of the probe intensity of the target region of the genome to that of the other portions of the genome. For example, a DNA library produced by cloning a particular chromosome (e.g. chromosome 7) can be used as a stain capable of staining the entire chromosome. The library contains both sequences found only on that chromosome, and sequences shared with other chromosomes. Roughly half the chromosomal DNA falls into each class. If hybridization of the whole library were capable of saturating all of the binding sites on the target chromosome, the target chromosome would be twice as bright (contrast ratio of 2) as the other chromosomes since it would contain signal from the both the specific and the shared sequences in the stain, whereas the other chromosomes would only be stained by the shared sequences. Thus, only a modest decrease in hybridization of the shared sequences in the stain would substantially enhance the contrast. Thus contaminating sequences which only hybridize to non-targeted sequences, for example, impurities in a library, can be tolerated in the stain to the extent that the sequences do not reduce the staining contrast below useful levels.

Kits Containing Probes of the Invention

This invention also provides diagnostic kits for the detection of chromosomal abnormalities at the regions disclosed here. In a preferred embodiment, the kits include one or more probes to the regions described herein. The kits can additionally include blocking probes, instructional materials describing how to use the kit contents in detecting the alterations. The kits may also include one or more of the following: various labels or labeling agents to facilitate the detection of the probes, reagents for the hybridization including buffers, a metaphase spread, bovine serum albumin (BSA) and other blocking agents, sampling devices including fine needles, swabs, aspirators and the like, positive and negative hybridization controls and so forth.

EXAMPLES

MATERIALS AND METHODS

Metastatic or primary tumor tissue was obtained from two groups of patients with metastatic prostate cancer (see Table 1). Group I consisted of 20 patients who had not been exposed to long term androgen deprivation or other therapies. Group II consisted of 11 patients with clinical disease progression despite long term androgen deprivation therapy (androgen independent disease).

Group I Tissue from Metastases. Eighteen of these twenty patients were initially thought to have tumors confined to the prostate but were later found have pelvic lymphatic metastases at the time of staging pelvic lymphadenectomy. Portions of the metastatic cancer tissue obtained at lymphadenectomy were used for this study. None of these eighteen had undergone androgen deprivation therapy, chemotherapy, or radiation therapy prior to this surgery. The remaining two samples were obtained from patients with prostate cancer metastatic to the bone. One of these patients (#375) underwent androgen deprivation therapy one month prior to bone biopsy. The other patient (#391) received no therapy prior to bone biopsy.

Considering these 20 patients together, the mean age at the time of tissue sampling was 61 years, with a range of 44–72 years. Five of the men are of African-American descent, the other 15 are Caucasian, with no more detailed ethnic data available. Mean serum PSA (Hybritech) one day to 20 weeks prior to pelvic node dissection or bone biopsy for the 20 men was 61 ng/ml, with a range of 3.3–250 ng/ml. Mean prostate biopsy Gleason score (Gleason, D. F., *Cancer Chemother Rep,* 50:125–8 (1966)) for the 18 men found to have pelvic metastases was 7, with a range of 4–9 (Table 1). Family history of prostate cancer was available for 12/20 patients, and was negative for all 12.

Precise histological control was achieved for all tissues studied in this group using the following protocol. Tissues not needed for histological diagnosis were snap frozen at −80° C. within 10–30 minutes after surgical removal. Serial cryostat sectioning was used to identify portions of the sample containing a lower fraction of tumor cells. These areas were removed from the tissue block by microdissection every 300 $\mu$M. The area of tissue remaining after microdissection varied from approximately 2×5 mm to 10×20 mm. The estimated tumor cell fraction (fraction of the sample composed of tumor cells as opposed to lymphocytes or stromal cells) was determined by visual estimation in 20 randomly selected fields examined at total magnification of 100× (Olympus Optical Co., Ltd., Japan) and averaged for all histological sections produced during serial sectioning (Table 1). DNA was obtained from between 200 and 1000 6$\mu$ sections for each case. If we estimate that one tumor cell is contained in every 1000 $\mu^3$ tissue volume, the samples studied consisted of DNA pooled from between $10^7$ and $10^9$ metastatic prostate cancer cells. DNA purification was performed as described previously (Bova, et al., *Cancer Res,* 53:3869–73 (1993)). Aliquots of the same DNA samples were used for both allelotyping and CGH. For both Southern and microsatellite analysis, noncancerous comparison DNA was prepared from pooled blood lymphocytes from each patient.

Group II Tissue from Androgen Independent Cases. These patients showed clinical disease progression despite long term androgen deprivation therapy. Four patients underwent transurethral resection for locally advanced tumor obstructing the bladder outlet, 6 patients underwent core biopsy of recurrent pelvic tumor after radical prostatectomy, and one patient suffered a scrotal skin metastasis. Thus, genetic analysis was performed on primary tumor in 4 cases, persistent or recurrent primary tumor in 6 cases, and metastatic tumor in one case.

Considering these 11 patients together, the mean age at the time of tissue sampling was 72 years, with a range of 43–96 years. All of these 11 patients are Caucasian, with no more detailed ethnic data available. Mean serum PSA at the time of diagnosis of metastatic prostate cancer was 272 ng/ml with a range of 14.9–1632 ng/ml. Mean Gleason Score was 7.6 with a range of 6–10.

Histological control was less precise for these tissues, since the estimated tumor cell fraction was not determined directly on the piece of tissue from which DNA was isolated. Instead, it was estimated from a histological section of a nearby piece of tissue removed during the same surgical procedure. Thus, the estimated tumor cell fraction listed in Table 1 is less precise than for Group I. DNA was isolated from fresh tissue brought immediately from the operating room or clinic by proteinase K dissection and phenol-chloroform-isoamyl alcohol extraction. Serial cryostat sectioning was not used.

Comparative Genomic Hybridization. CGH was performed as described previously (Cher, et al., *Genes Chromosom Cancer,* 11:153–162 (1994)) with the modification that DNA was labeled by direct incorporation of fluorochrome-linked nucleotides. Briefly, tumor DNA (0.5–1 $\mu$g) was labeled by nick translation in the presence of 20 $\mu$M daTP, dCTP, dGTP and FITC-12-dUTP (NEN Research Products, Boston, Mass.). Normal DNA, isolated from the lymphocytes of a laboratory volunteer, was labeled in an identical fashion using Texas Red-5-dUTP (NEN Research Products). Hybridization with 0.2–1.0 $\mu$g of labeled tumor and normal DNA and 10 $\mu$g of Cot-1 DNA was performed on metaphase spreads from a normal donor's lymphocytes for 2–3 days, the slides were washed, dehydrated in ethanol, and the metaphase spreads were counterstained with 0.1 $\mu$M DAPI.

Five to 10 fluorescence microscopic metaphase images of each color were acquired for each tumor/normal hybridization; 4 to 5 images were chosen for quantitative analysis. For each metaphase image, green (tumor) and red (normal) fluorescence intensity values were calculated as described previously (Cher, et al., *Genes Chromosom Cancer,* 11:153–162 (1994); Kallioniemi, et al., *Genes Chromosom Cancer,* 10:231–43 (1994)). The green and red fluorescence intensity values along each chromosome were then assigned to data channels appropriate for their location in the genome. There were 1247 data channels extending along the length of the genome from 1pter to Yqter with the number of channels for each chromosome assigned to a fixed value based on the relative lengths of the chromosomes (Morton, N.E., *Proc Natl Acad Sci* USA, 88:7474–6 (1991); Lucas, et al., *Cytometry,* 8:273–9 (1987)). Thus channels 1 to 100 contained fluorescence intensities measured for chromosome 1, channels 101–197 contained intensities for chromosome 2, etc. Each metaphase image generally yielded intensity values of each color for both members of all autosome pairs and one intensity value of each color for chromosome X and chromosome Y. Fluorescence intensity of each color was normalized for a given metaphase and the ratios of green/red were calculated for each data channel for each chromosome image. Green/red fluorescence intensity ratio distributions (mean and standard deviation) were then calculated for each data channel taking into account the ratios from every chromosomal image in every metaphase that was analyzed. In general, averages over 7 images of each autosome were combined (range 4–10) to provide a fluorescence intensity ratio profile distribution along the genome for each tumor.

Quantitative Analysis by CGH. In order to quantitatively analyze CGH data, we compared results from tumor/normal hybridizations with those from normal/normal controls. Thus, we performed 5 two-color hybridizations involving only normal DNA labeled both green and red to be used as controls for comparison with tumor/normal hybridizations. CGH was performed using the same methodology as that used for tumor DNA. For each of these control hybridizations, 4 metaphase images were analyzed resulting in up to 8 images for each autosome and 4 images for each sex chromosome. As expected, the green/red ratios were centered around 1.0 along the length of the genome for each of these control hybridizations. However, close examination of the ratios revealed that many genomic regions consistently showed green/red ratios slightly different from 1.0. For example, the region corresponding to chromosome 1p32-1 pter showed an average green/red ratio of 1.07, the region corresponding to chromosome 19 showed an average ratio of 1.08, and the region corresponding to chromosome 4q showed an average ratio of 0.952. The cause of these consistent deviations in the green/red ratios in the normal/normal control hybridizations was unknown. We suspect that hybridization properties are slightly altered by incorporation of conjugated uridine into the probe DNA, and these hybridization differences are revealed by slight variations in particular regions of the metaphase chromosomes, perhaps due to protein/DNA interactions or chromosomal structure. Additionally, standard deviations of the ratios tended to vary from region to region. For example, standard deviations tended to increase near chromosomal telomeres and centromeres. At the centromeres this can be explained by the fact that unlabeled Cot-1 DNA was added to block non-specific repetitive DNA hybridization by the labeled DNAs, and since large amounts of repetitive DNA is present at the centromeres, a decreased intensity of both green and red fluorescence resulted in these regions. The decreased intensity of both fluorescence colors resulted in lower precision in the intensity measurements and ratio calculations. At the telomeres there appears to be a slight uncertainty in the definition of the exact terminus as determined by the image analysis algorithm due to the fact that there is a large area of local background which causes local decrease in the chromosomal image intensity for both colors. As with the centromeric regions, this resulted in a lower precision in intensity measurements at the telomeres.

Data from these 5 control normal/normal hybridizations, obtained under the same experimental conditions as for the tumor/normal hybridizations, were combined to model the behavior of the ratios when no genetic alterations were present. Therefore, each of the 1247 data channels along the genome in the control hybridizations was assigned a specific green/red fluorescence intensity ratio distribution. We then compared the green/red distributions for each tumor/normal hybridization to those for the combined pool of control normal/normal hybridizations. A t-statistic was calculated independently for each channel along the genome to test whether the mean ratio for a tumor/normal hybridization was significantly different from the mean ratio for the control normal/normal hybridizations. At each of the 1247 data channels, larger absolute values of t indicated higher statistical confidence that a chromosomal alteration was truly present. Positive values of t indicated gain of genetic material in the tumor DNA while negative values of t indicated loss of genetic material. Finally, centromeric and heterochromatic regions were excluded from interpretation since hybridization in these regions is imprecise (Kallioniemi, et al., *Genes Chromosom Cancer,* 10:231–43 (1994)).

In quantitative CGH analysis, a threshold t, value must be chosen in order to use the t-statistic for defining whether a ratio at any point along the genome indicates a significant gain or loss of genetic material in any given tumor DNA sample. The value of the threshold directly affects the sensitivity and specificity of CGH analysis and should be set according to the goals of the study. To define this threshold for our study, we calculated the statistics for each of the normal/normal control hybridizations by comparing each one to the complete set of 5 control hybridizations. During this analysis, we found that smoothing the normal/normal ratio variances by averaging over several contiguous channels prior to formation of the t-statistic, greatly reduced the number of false "gains" and "losses" in the control hybridizations. Thus, we adopted this procedure for all our t-statistical calculations, and the variance in each data channel for the normal/normal elements in the analysis was averaged with those of 5 contiguous channels on each side of that channel. Within 5 channels of chromosomal termini and centromeres, the number of contiguous channels in this averaging was decreased systematically by averaging only to the terminus or centromere. Using this procedure for t-statistical evaluation, the t values for all of the control hybridizations were near zero with very few elevated positive or negative values (FIG. 1). For example, 99% of t values for the control hybridizations were between −1.36 and 1.36. For this study, we chose a threshold of $|t|>1.6$ for the definition of losses and gains. At this threshold level less than 0.3% (17 out of 6235) $|t|$ values from the 5 normal/normal control hybridizations were over the threshold. Based on the curve shown in FIG. 1, lowering the t threshold would result in a rapid loss of specificity (increase false-positives); also, this threshold level resulted in a high level of sensitivity for the detection of chromosomal alterations based on the high level of concordance with the independently performed allelotyping experiments (see Results).

Allelotyping. For the 20 Group I metastatic tumors, Southern analysis was carried out at 29 loci on 19 chromosome arms, and microsatellite analysis was performed at 24 loci on 7 arms. Many of the loci were chosen because they fell within regions previously found to be relevant to prostate cancer. In particular, we tested multiple loci on the following chromosome arms (chromosome arm/number of loci compared): 2q/3; 8p/9; 10q/5; 13q/12; 16q/5; 18q/3. In addition, 12 other chromosome arms were represented with one or two loci each.

Loci studied by Southern analysis were D1S57, D1S74, D2S44, D2S48, D2S50, D2S53, RAF1(3p), D4S125, D6S44, D7S150, KSR (8p), MSR (8p), D8S140, D8S220, D8S194, D8S39, IFNB1 (9p), D10S25, D10S28, D13S1, D13S2, D16S7, CEPT-A/B (16q), TAT (16q), D17S5, D17S34, D17S74, DCC (18q), and DYZ4 (Y). Southern analysis was performed as described in Bova, et al., *Cancer Res,* 53:3869-73 (1993).

Loci studied by microsatellite analysis were D2S123, APC (5q), D8S201, LPL (8p), D8S261, D8S264, D10S190, D10S192, D10S201, D10S217, D13S115, D13S121, D13S134, D13S146, D13S147, D13S152, D13S170, D13S171, D13S175, D13S309, D16S26, D16S402, D18S61, and D18S69 (Weissenbach, et al., *Nature,* 359:794-801 (1992)). Microsatellite analysis was performed as described in Bova, et al., *supra.*

Allelic loss using Southern and microsatellite analysis was defined as the absence of one allele in prostatic tumor DNA compared to the noncancerous paired control DNA as defined by inspection of the autoradiograph. In some cases, when there was residual signal from contaminating normal tissue, densitometry was used for analysis. A sample was scored as having allelic loss if approximately 60% reduction was present in the diminished allele compared to its normalized retained counterpart.

Only one region (chromosome 8q) showed allelic gain by Southern blotting. Allelic gain using probe MCT 128.2 (8q) was defined as an increase in intensity of greater than 100% of one of two alleles present in tumor samples, or intensity differences of greater than 100% between tumor and normal alleles in homozygous cases when prior probing of the same blots demonstrated equal loading of DNA in tumor and normal lanes. Allelotyping measurements were performed and analyzed in a blinded fashion with respect to the CGH findings.

RESULTS

Hybridization quality. We found that the direct labeling technique of incorporation of fluorochrome-linked nucleotides into genomic DNA resulted in higher quality hybridization when compared with the older technique of detection using fluorochrome-linked secondary reagents (Cher, et al., *Genes Chromosom Cancer,* 11:153-162 (1994)). By fluorescence microscopic examination this increase in quality could be seen as less granular images with sharper transitions of color at the termini of losses and gains. Additionally image analysis tracings of the fluorescence ratios were smoother, such that when data from multiple images were combined, the standard deviations of the fluorescence ratios were reduced.

Figure 2:
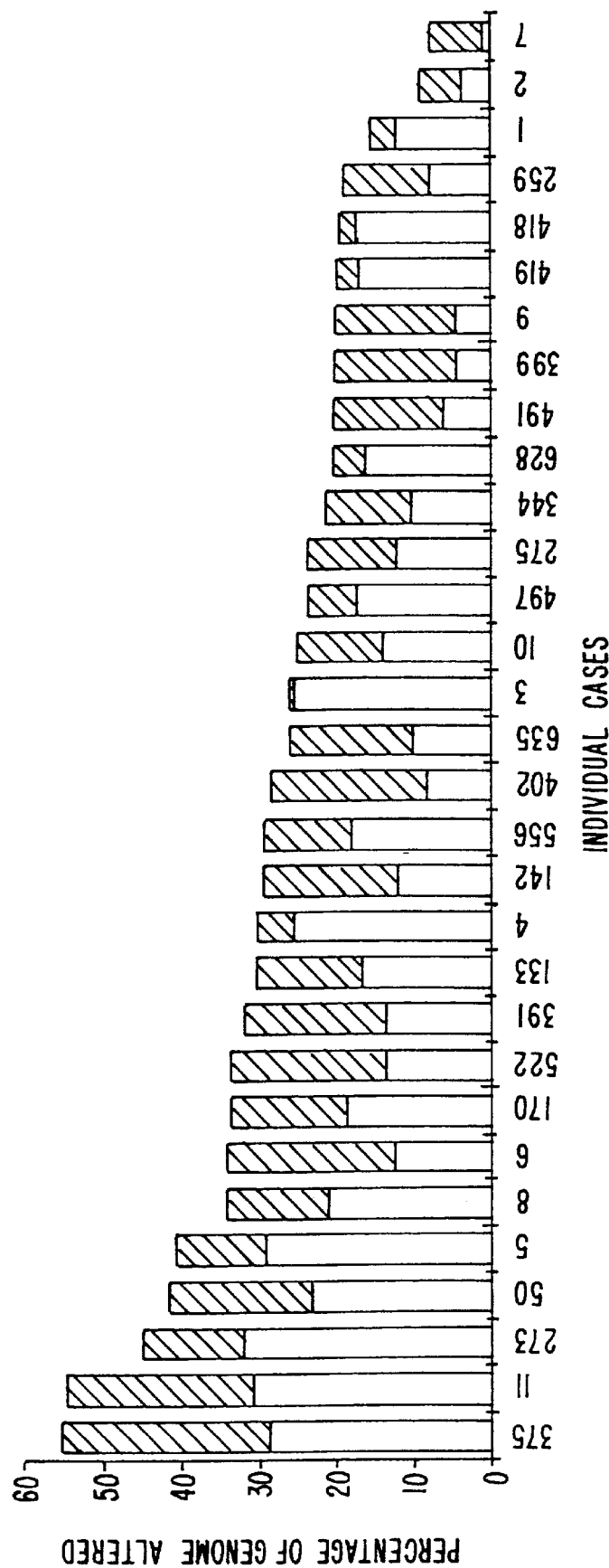
FIG. 2 is a bar graph showing percentage of the genome with alterations. The percentage of the genome gained (shaded) and lost (solid) is shown for each tumor specimen.

CGH using t threshold 1.6. On all tumor DNA samples were applied quantitative CGH as described in Material and Methods, using t thresholds of +1.6 for gains and −1.6 for losses. With this analytical approach, all tumors in both groups of specimens displayed some DNA alterations (losses or gains relative to average DNA copy number). The proportion of the genome with either losses or gains was calculated for each tumor and is depicted in FIG. 2. It is clear that a large fraction of the genome appears altered in most specimens. Thus, the high level of specificity obtained by using $|t|>1.6$ did not sacrifice the sensitivity to detect changes. It should also be noted that the three tumors with the least altered genomes are from group II. This most likely reflects lower tumor cell fraction in these samples as shown in Table 1. Samples displayed many different relative proportions of gains and losses, with no specific pattern among samples in each group. Overall, there were nearly equal proportions of the genome involved in gains as in losses: Group I averaged 15% of genome gained and 14% lost; Group II averaged 16% gained and 11% lost.

Figure 3:
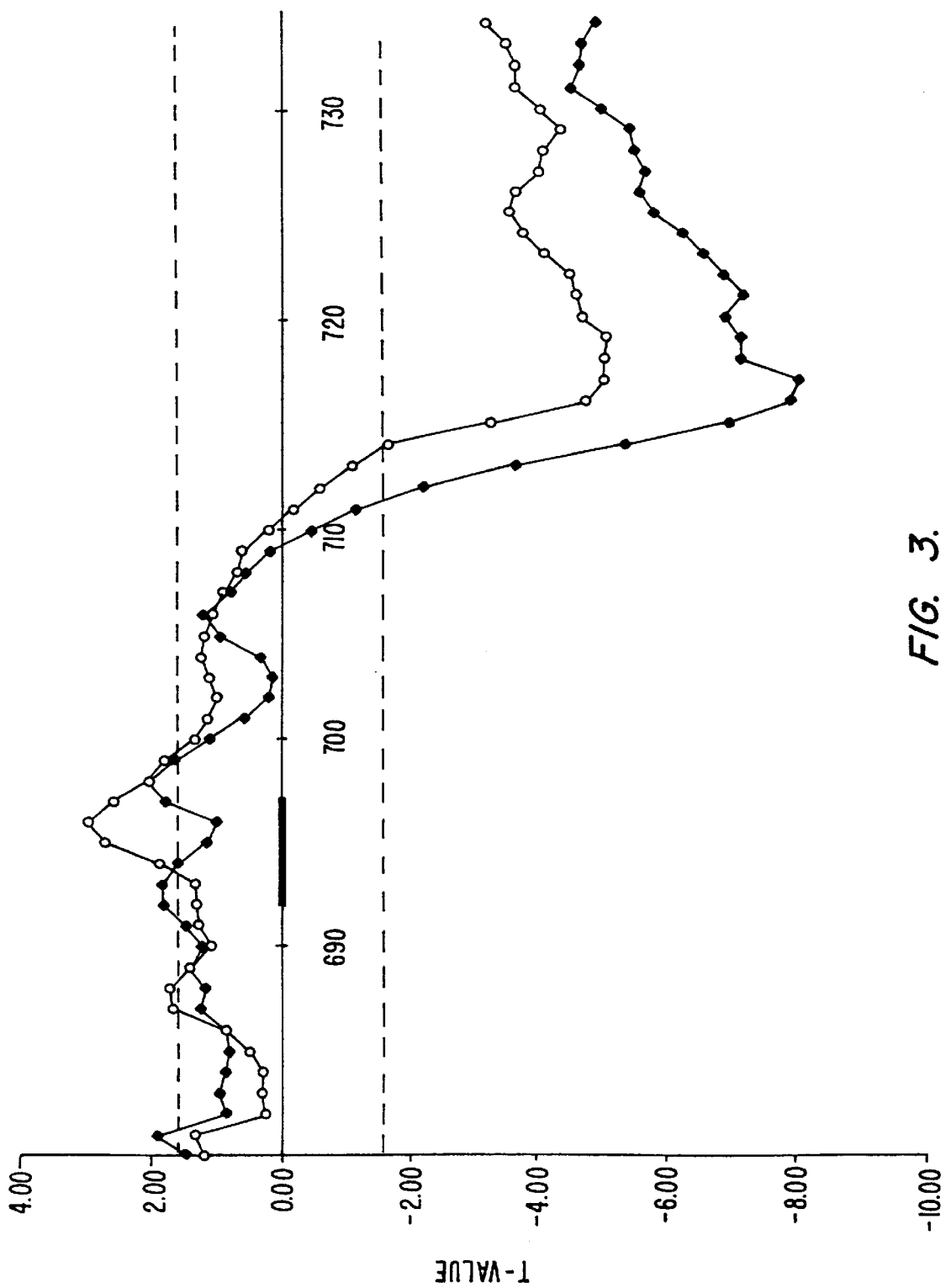
FIG. 3 is a graph showing comparison of two CGH analyses on a single DNA specimen. One tumor DNA specimen was analyzed by CGH analysis two times in a blinded fashion. The entire CGH procedure, including labeling, hybridization, and analysis was performed independently for each specimen. Each line shows t values for the 55 data channels of chromosome 10 for a single run. Threshold of 1.6 is shown by dotted lines. X-axis shows data channel number (of 1247 total) and heavy line represents region of centromere.

To test the reproducibility of this new CGH method, one tumor DNA sample was submitted and analyzed twice in a blinded fashion. Using the t-statistic method, regions of loss and gain were determined independently on these two specimens. DNA from this particular tumor (#50) showed a large number of alterations, with 26% of the genome showing a significant gain and 21% of the genome showing a significant loss. In comparing the results of the two independent analyses, 89% of the 1247 data channels indicated identical locations for gains, losses or no change. The primary differences in the two data sets are at the termini of alterations, where t values are changing rapidly with channel number. An illustration of this comparison is shown in FIG. 3, where the t values in the data channels for chromosome 10 from each of the two runs are plotted, and the t-thresholds are indicated. In this illustration both the relative agreements and disagreements can be viewed. The two data sets agree in 84% of the data channels (46/55) with the majority of the differences occurring in small regions (one or two contiguous channels). This duplicate determination illustrates the power of CGH to present reproducible locations of gains and losses over the entire genome and also displays its weakness as a lack of high resolution in defining the location of alterations.

Figure 4:
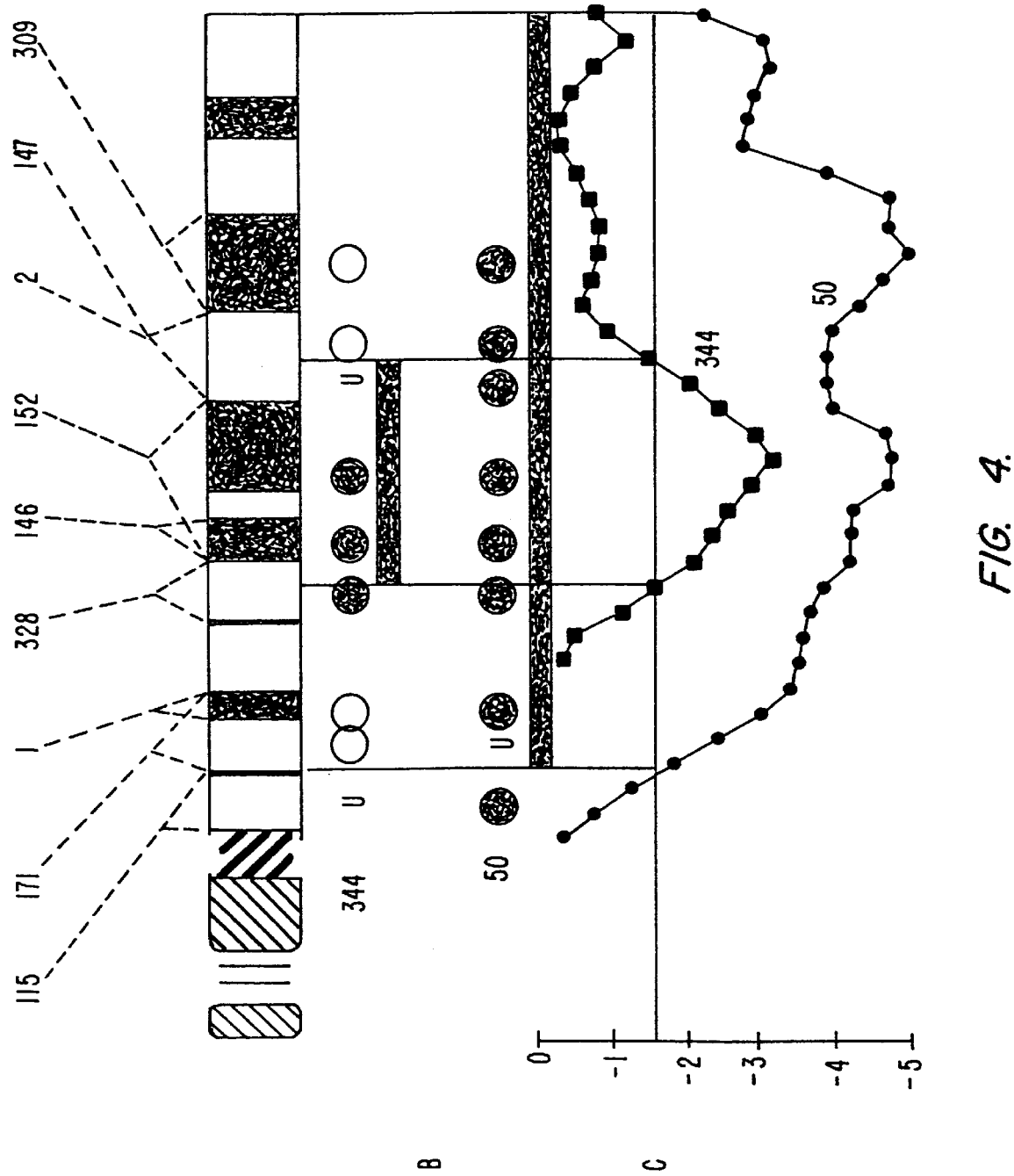
FIG. 4 is ideogram showing correlation of CGH and allelotyping data. Data from two representative tumors (#50 and #344) are depicted. Microsatellite and restriction fragment length polymorphism analysis at 9 separate loci on chromosome 13q was used. Mapped locations of each polymorphism (listed by D13S number) are indicated by the dashed lines leading to the ideogram. The CGH interpretation for each tumor is shown by the shaded bar indicating the length and position of losses in each tumor with respect to the ideogram. Allelotyping results are depicted as: open circles=retained; closed circles=lost; U=uninformative. The calculated t-statistics are shown as continuous tracings for both tumors. The X axis is drawn at t=−1.6, and the vertical lines connecting the tracings to the ideogram indicate the termini of the chromosome 13q losses found in these two tumors.
Figure 5A:
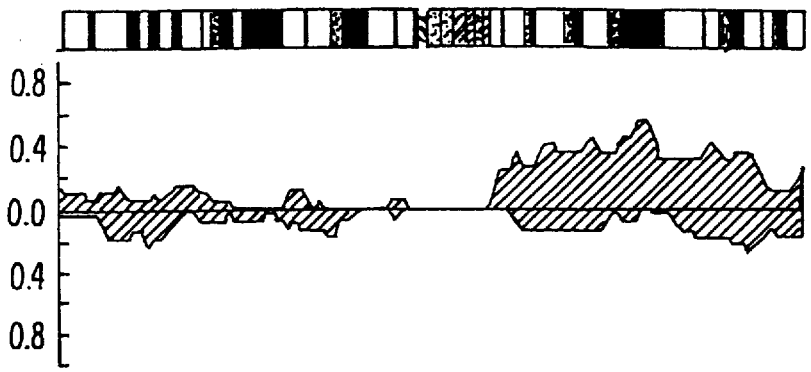
FIG. 5 shows the relative frequency histograms of genetic alterations in DNA from Group I specimens. The relative frequency of gains and losses is shown as a region-specific histogram along each chromosome arm. The y-axis shows the proportion of specimens (of the 20 metastases analyzed) with t>1.6 above the central axis and with t<−1.6 below the central axis. Centromeres and heterochromatic regions were excluded from analysis. Histograms are matched to ideograms of each chromosome based on the data channels which contain the appropriate data distributed along the length of each chromosome. Chromosome identification numbers appear in the upper left of each panel.
Figure 5B:
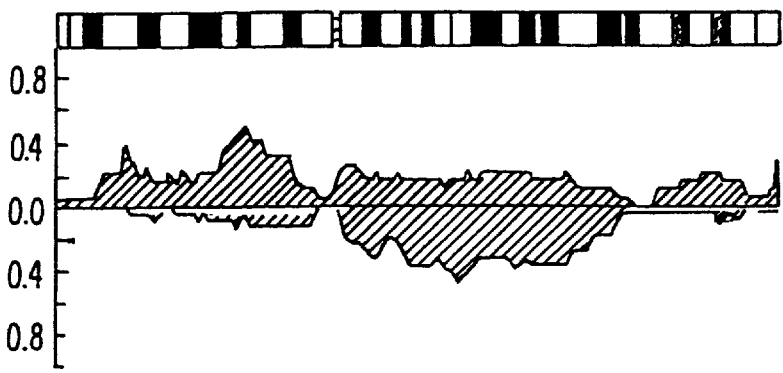
Figure 5C:
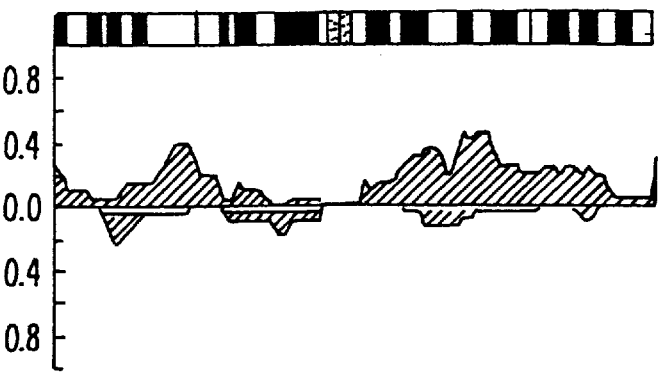
Figure 5D:
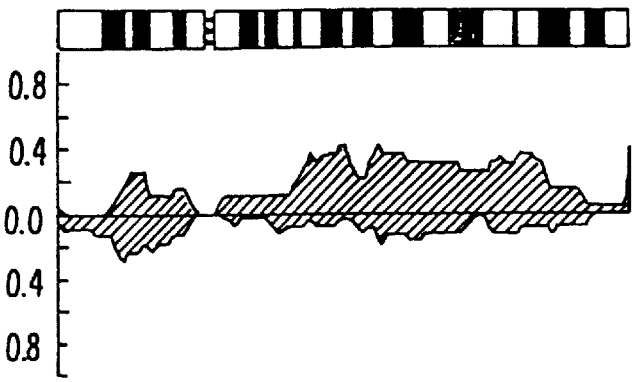
Figure 5E:
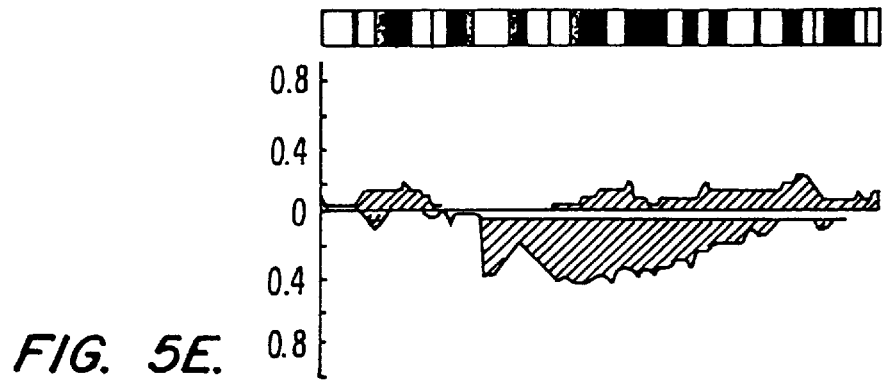
Figure 5F:
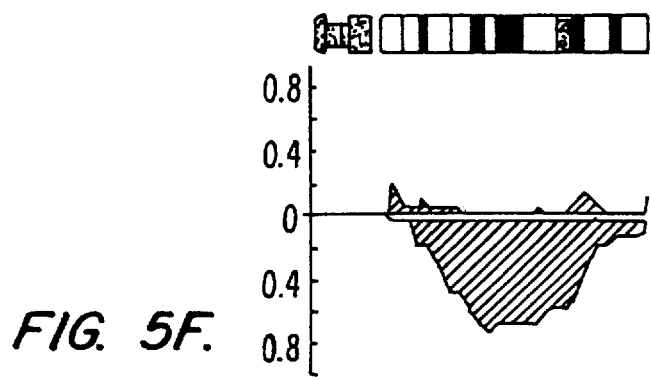
Figure 5G:
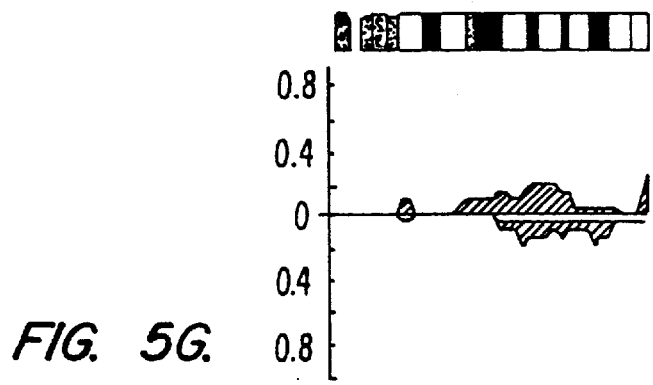
Figure 5H:
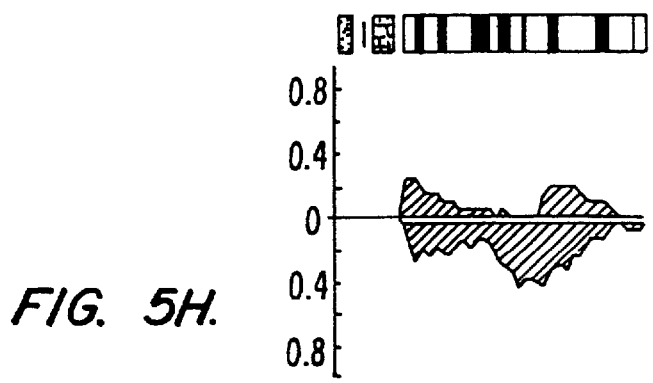

CGH Concordance with Allelotyping. To validate this quantitative statistical approach to CGH analysis, we compared CGH with allelotyping results on each of the 20 Group I tumor specimens. FIG. 4 shows an example of the method of comparison for two tumors on one chromosome.

Overall, the allelotyping studies resulted in 280 informative results at 49 different loci. A summary of the comparisons to CGH is shown in Table 2. Of the 280 informative results obtained with allelotyping, 44 instances could not be compared to CGH due to imprecise physical mapping of the Southern probes or microsatellite polymorphisms relative to the termini of CGH-defined alterations. Of those that could be compared, discordant results occurred in only 18/236, Twelve of these 18 disagreements occurred in instances where CGH indicated a loss but the alleles appeared balanced. The level of agreement using the K statistic (Cohen, J., *Educat Psychol Meas,* 20:37-46 (1960)), which takes into account agreement that might occur by chance alone, is K=0.83 (95% confidence interval is 0.70–0.95), with no difference in the level of agreement of CGH with Southern or microsatellite analysis.

Frequency of Regional Chromosomal Alterations: Group I. To define the general tendencies of DNA alterations in the genome of untreated tumor metastases, we created a point-by-point histogram along all chromosome arms showing the region-specific frequency of losses and gains in this series of 20 untreated prostatic metastases. FIG. 5 shows the frequency of occurrence of $|t|>1.6$ for each data channel plotted relative to an ideogram of each chromosome. It shows that the following 9 chromosomal arms showed loss (in at least one region of each arm) in more than 40% of the cases: 8p (80%), 13q (75%), 16q (55%), 2q (50%), 10q (50%), 17p (50%), 5q (45%), 6q (45%) and 15q (45%) and the following 7 chromosomal arms showed gain (in at least one region of each arm) in more than 40% of the cases 8q (85%), 1q (55%), 11p (55%), 2p (50%), 3q (45%), 7q (45%), and 9q (45%) (FIG. 5).

Close examination of the frequency histograms in FIG. 5 reveals that some of the frequently altered regions contain smaller sub-regions with higher frequencies of alteration than adjacent regions. For example, losses on chromosome 13 increase in frequency continuously from 13q11 to q21.1, remain at about 70% through 13q21.1-q22 and decrease continuously in frequency from 13q22 to q35. Thus, the region 13q21.1.q22 displays the highest chance of containing an important prostate tumor suppressor gene. Detailed analysis of such regions with a technique of higher resolution (such as PCR microsatellite allelotyping) is required to define the region more precisely.

FIG. 5 shows other chromosomal regions which are altered in a somewhat lower proportion of Group I tumors. The most frequent of these are 3p gain (40%), 4p gain (40%) and 11p loss (30%). Interestingly, there are 12 chromosomal arms where both losses and gains were detected in at least 20% of the cases. In 7 of these 12 arms the regions of loss and gain do not overlap and it could be that recessive and dominant oncogenes are distributed throughout these regions. Again, more precise localization of each region would address this question better.

Finally, FIG. 5 shows a modest frequency of alterations (5–20%) in almost all areas of the genome suggesting that some clonal chromosomal alterations arise randomly and are maintained in proliferating prostate cancer cells.

Frequency of Chromosomal Alterations: Group II. Eleven specimens from patients with disease progression despite long term androgen deprivation also were analyzed by CGH. As with Group I specimens, we performed a point-by-point histogram analysis along all chromosomal arms showing the region-specific frequency of alterations. Overall, the results revealed a very similar pattern of chromosomal alterations as were seen for DNA isolated from Group I tissues. In particular, the most commonly detected changes were a loss in chromosome 8p, a gain in chromosome 8q, and a loss in chromosome 13q. Histograms obtained for these chromosomes of Group II samples (FIG. 6) appear quite similar to those obtained for Group I (FIG. 5). In order to test for differences in chromosomal alterations between Group I and Group II specimens, we constructed 2×3 contingency tables at each of the 1247 data channels along the genome. Each table contained the number of specimens from each of the two groups that had either a loss, a gain, or no change at each data channel. We then tested whether there was a difference in the frequency of gains or losses for each table using Fisher's exact test. The result of these analyses showed no more than the expected number of significant differences (at p<0.05) based on performing a large number (1247) of tests.

FIG. 7 shows a summary of the frequency of gains and losses in regions of the genome which show alterations in many of the samples. None of the differences between the two groups is statistically significant (p>0.1). One may conclude from these data that most chromosomal alterations occur without androgen deprivation therapy.

Groups I and II Combined. Since the data sets for the two groups of tumors were not significantly different, we combined them and calculated the overall frequency of gain and loss at each channel (FIG. 7). For other subgroup comparisons of chromosomal alteration frequency, the combined data set was divided into groups based on younger or older patient age, higher or lower serum PSA, and ethnic group (African American vs. Caucasian). Similar contingency table analyses were carried out as described above. No regional differences in the frequency of gains or losses were detected among the groups defined by patient age or serum PSA.

In contrast, we did find an indication of increased frequency of gains in the region of 4q25-q28 in African Americans. With a careful comparison of frequency histograms (such as those displayed in FIGS. 5 and 6) this region was the only one in which all 5 blacks showed an alteration. We found that the entire band 4q27 showed a significant gain in samples from 5/5 African Americans as compared to 3/26 Caucasians. In addition, a larger region of 6 contiguous data channels in 4q27q28 showed gain in at least 4/5 samples from African Americans as compared to fewer than 4/26 samples from Caucasians (Fisher's exact p<0.01 for each comparison). We determined the statistical significance of this finding by randomly selecting subsets of 5 tumors, from among the total of 31, and repeating the contingency table analyses for the entire genome, each time comparing the subset of randomly selected 5 with the remaining 26. We found that only 5% of these samples contained a section of 6 contiguous data channels with Fisher's exact p<0.01 (based on 1000 randomly formed subsets). We also found that only 0.5% of theses randomly generated subsets showed "significant" gains on chromosome 4. In the comparison of African Americans to Caucasians, no other regions in the genome differed significantly, although statistical power is low due to the small number of blacks in this study.

TABLE 1

Clinical data on patients from whom tissue was taken for analysis.
Abbreviations: PSA: prostate specific antigen; c: Caucasian; a: African-American;
LN: pelvic lymph node; met: metastasis; bx: biopsy; TURP: transurethral resection of prostate.

|  | Specimen Number | Age | Race | Serum PSA | Primary Tumor Gleason Score | Tissue Studied | Estimate Tumor Cell Fraction |
|---|---|---|---|---|---|---|---|
| Group I | 50 | 69 | c | 21. | 7 | LN met | 0.9 |
|  | 133 | 70 | c | 69.7 | 9 | LN met | 0.85 |
|  | 142 | 61 | c | 26.2 | 9 | LN met | 0.95 |
|  | 170 | 57 | c | 3.3 | 4 | LN met | 0.9 |
|  | 259 | 69 | c | 32.3 | 7 | LN met | 0.95 |
|  | 273 | 53 | c | 29. | 7 | LN met | 0.85 |
|  | 275 | 66 | c | 123. | 6 | LN met | 0.65 |
|  | 344 | 60 | c | 29.7 | 7 | LN met | 0.85 |
|  | 375 | 54 | c | 12. | 9 | bone met[2] | 0.75 |
|  | 391 | 57 | c | 16.9 | 5 | bone met | 0.95 |
|  | 399 | 65 | c | 23.6 | 7 | LN met | 0.9 |
|  | 402 | 56 | c | 41.3 | 7 | LN met | 0.9 |
|  | 418 | 68 | a | 21.4 | 8 | LN met | 0.7 |
|  | 419 | 57 | a | 102. | 5 | LN met | 0.95 |
|  | 491 | 72 | a | 250. | 8 | LN met | 0.75 |
|  | 497 | 45 | c | 130. | 8 | LN met | 0.65 |
|  | 522 | 57 | c | 13.3 | 7 | LN met | 0.9 |
|  | 556 | 66 | c | 9.2 | 8 | LN met | 0.85 |
|  | 628 | 44 | a | 235. | 7 | LN met | 0.85 |
|  | 635 | 65 | a | 31. | 6 | LN met | 0.9 |
| Group II[b] | 1 | 75 | c | 299. | 7 | prostate bx | unknown[c] |
|  | 2 | 96 | c | 142. | 7 | TURP | 0.65 |
|  | 3 | 65 | c | 1632. | 9 | prostate bx | 0.5 |
|  | 4 | 67 | c | 14.9 | 7 | prostate bx | 0.5 |
|  | 5 | 75 | c | 209. | 9 | TURP | 0.9 |
|  | 6 | 85 | c | 105. | 9 | TURP | 0.8 |
|  | 7 | 58 | c | 58.8 | 6 | prostate bx | 0.5 |

TABLE 1-continued

Clinical data on patients from whom tissue was taken for analysis.
Abbreviations: PSA: prostate specific antigen; c: Caucasian; a: African-American;
LN: pelvic lymph node; met: metastasis; bx: biopsy; TURP: transurethral resection of prostate.

| Specimen Number | Age | Race | Serum PSA | Primary Tumor Gleason Score | Tissue Studied | Estimate Tumor Cell Fraction |
|---|---|---|---|---|---|---|
| 8 | 78 | c | 22. | 7 | prostate bx | 0.6 |
| 9 | 78 | c | 232. | 7 | prostate bx | 0.4 |
| 10 | 74 | c | 106. | 6 | skin met | 0.7 |
| 11 | 43 | c | 173. | 10 | TURP | 0.95 |

[a]Patient received one month of androgen deprivation therapy prior to tissue sampling.
[b]Group II tumors progressed clinically while on androgen deprivation therapy. For these tumors, histological analysis was performed on adjacent surgical samples.
[c]Slides could not be located.

TABLE 2

Correlation of CGH findings with allelotyping results.
Results from the two techniques were compared at each informative southern or microsatellite locus.

| CGH Result | Allelotype Result (Southern/Microsatellite) | | |
|---|---|---|---|
| | imbalance | balance | total |
| loss or gain[a] | 68 | 12 | 80 |
| no alteration | 6 | 150 | 156 |
| totals | 74 | 162 | 236 |

[a]In 3 of 4 instances of allelic imbalance on chromosome 8q, southern analysis was able to detect a gain rather than a loss; by CGH, all alterations on chromosome 8q were gains. All other allelic imbalances were losses by CGH. Applying the K Statistic (30); K = 0.83 (0.70–0.95 is 95% confidence interval).

DISCUSSION

The goal of this study was to gain a pan-genomic view of the locations and frequencies of regional chromosomal alterations in prostate cancer. Genetic events leading to the initiation of prostate cancer are of obvious importance, but since the majority of prostate cancers never metastasize (Dhom, G., J Cancer Res Clin Onc, 106:210-18 (1983)), additional genetic events must be involved in the progression to lethal metastatic prostate cancer. By their proven ability to metastasize and their relative purity, the tumors studied here provided excellent material in which to define genetic alterations potentially involved in both initiation and progression of prostate cancer. Application of a new method for interpretation of fluorescence intensity values has led to a standardized CGH analysis, allowing detection and mapping of these genetic alterations based on statistical comparisons of intensity ratios relative to control experiments.

In 20 of the 31 cases studied, CGH analysis was corroborated with parallel Southern and microsatellite analysis of allelic imbalance on the same DNA. The good agreement between these two analytical techniques (K=0.83) provides assurance that the new, standardized CGH analysis is demonstrating high sensitivity and specificity.

Overall Genomic Considerations. The frequency of copy number alterations found in DNA samples from prostate cancer tissue studied here seems rather large when viewed in light of flow cytometry and other ploidy studies, which have shown that metastatic prostate cancers are diploid in nearly 50% of the cases (Stephenson, et al., Cancer Res, 47:2504-7 (1987)). However, the data presented here suggest that equal proportions of relatively small regions of the genome are often lost or gained in many tumors resulting in an overall balance of genetic material and normal ploidy determination. In addition, when tumors are tetraploid, changes in copy number among different regions of the genome will be small relative to the total cellular DNA content. For example, tumor 399 was determined to be tetraploid on Feulgen staining and image analysis (data not shown). Thus the losses and gains detected by CGH must be interpreted from a baseline of 4 allelic copies. Losses and gains were detected in approximately 5% of and 18%, respectively, of the 1247 data channels across the genome. Although we were unable to determine exactly how many copies were lost or gained for each of the individual alterations, the data support the view that metastatic prostate cancers do contain critical DNA alterations which may be not be detectable when measuring gross DNA content. Since ploidy has been reported to be of independent prognostic value in some prostate cancer studies (Shankey, et al., Cytometry, 14:497-500 (1993)), we would suggest that ploidy measurements plus CGH or allelotyping analysis could provide improved tumor-specific prognostic information.

The results provided here indicate that most regions of the genome are altered in at least 5 percent of advanced prostate cancer cases. These seemingly random alterations would not have been detected had they not been clonally present in a significant number of cells in the tissues from which DNA was extracted. We presume that chromosomal regions with low frequency of alteration occur as a result of random genetic instability of advanced cancer, and they probably do not contain genes important to the aggressive phenotype.

In the present study gains were present as often as losses. However, the gains detected here were relatively low level in red/green fluorescence ratio and generally involved large regions or whole chromosome arms. No short, high level amplifications suggestive of single oncogene amplification were found such as those described for breast cancer (Kallioniemi, et al., Proc Natl Acad Sci USA, 91:2156-60 (1994)). Our results indicate a more subtle shift in gene copy numbers which correlates with earlier reports on relatively low levels of amplification in prostate cancer (Visakorpi, et al., Nature Genetics, 9:401-6 (1995); Bova, et al., Cancer Res, 53:3869-73 (1993); Van Den Berg, et al., Clin Ca Res, 1:11-18 (1993); Brothman, et al., Cancer Res, 50:3795-803 (1990)).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of screening for the presence or absence of prostate cancer cells in a sample, the method comprising:

contacting a nucleic acid sample from a human patient with a probe which binds selectively to a target polynucleotide sequence on a chromosomal region in which copy number is increased in prostate cells and is selected from the group consisting of 1q, 2p, 3p, 6p, and 17q, wherein the probe is contacted with the sample under conditions in which the probe binds selectively with the target polynucleotide sequence to form a stable hybridization complex; and detecting the presence or absence of a hybridization complex, thereby screening for the presence or absence of prostate cancer cells in the sample.

2. The method of claim 1, wherein the chromosomal region in which copy number is increased is 1q.

3. The method of claim 1, wherein the chromosomal region in which copy number is increased is 2p.

4. The method of claim 1, wherein the chromosomal region in which copy number is increased is 3p.

5. The method of claim 1, wherein the chromosomal region in which copy number is increased is 6p.

6. The method of claim 1, wherein the chromosomal region in which copy number is increased is 17q.

7. The method of claim 1, wherein the chromosomal region in which copy number is increased is from about 1q21.3 to about 1q42.3.

8. The method of claim 1, wherein the chromosomal region in which copy number is increased is from about 2p12 to about 2p23.

9. The method of claim 1, wherein the chromosomal region in which copy number is increased is from about 3p14.1 to about 3p22.

10. The method of claim 1, wherein the chromosomal region in which copy number is increased is from about 17q21 to about 17qter.

11. A method of screening for the presence or absence of prostate cancer cells in a sample, the method comprising:

contacting a nucleic acid sample from a human patient with a probe which binds selectively to a target polynucleotide sequence on a chromosomal region at about 17q12 from the oncogene erb B-2, wherein the probe is contacted with the sample under conditions in which the probe binds selectively with the target polynucleotide sequence to form a stable hybridization complex; and detecting the presence or absence of a hybridization complex, thereby screening for the presence or absence of prostate cancer cells in the sample.

12. The method of claim 1 or 11, wherein the detecting the presence or absence of the hybridization complex is carried by fluorescence in situ hybridization.

* * * * *